United States Patent
Hennings et al.

(10) Patent No.: US 8,448,644 B2
(45) Date of Patent: *May 28, 2013

(54) SONIC ENDOVENOUS CATHETER

(75) Inventors: David R. Hennings, Roseville, CA (US); David J. Fullmer, Roseville, CA (US); Craig Lindsay, Roseville, CA (US); Eric B. Taylor, Roseville, CA (US); Robert A. Weiss, Hunt Valley, MD (US)

(73) Assignee: CoolTouch Incorporated, Roseville, CA (US)

( * ) Notice: Subject to any disclaimer, the term of this patent is extended or adjusted under 35 U.S.C. 154(b) by 1341 days.

This patent is subject to a terminal disclaimer.

(21) Appl. No.: 11/928,624

(22) Filed: Oct. 30, 2007

(65) Prior Publication Data

US 2008/0275380 A1    Nov. 6, 2008

Related U.S. Application Data

(60) Provisional application No. 60/864,101, filed on Nov. 2, 2006.

(51) Int. Cl.
*A61B 19/00* (2006.01)
*A61B 18/18* (2006.01)
*A61N 5/06* (2006.01)

(52) U.S. Cl.
USPC ............... 128/898; 606/3; 606/15; 607/89

(58) Field of Classification Search
USPC ............. 128/898; 606/3, 7, 15; 607/88–89
See application file for complete search history.

(56) References Cited

U.S. PATENT DOCUMENTS

| | | | |
|---|---|---|---|
| 4,920,954 A * | 5/1990 | Alliger et al. | 606/128 |
| 5,380,273 A * | 1/1995 | Dubrul et al. | 604/22 |
| 5,498,236 A * | 3/1996 | Dubrul et al. | 604/22 |
| 5,713,848 A * | 2/1998 | Dubrul et al. | 604/22 |
| 5,789,755 A | 8/1998 | Bender | |
| 5,820,626 A | 10/1998 | Baumgardner | |
| 5,885,274 A | 3/1999 | Fullmer et al. | |
| 5,976,123 A | 11/1999 | Baumgardner et al. | |
| 6,028,316 A | 2/2000 | Bender | |
| 6,117,335 A | 9/2000 | Bender | |
| 6,200,466 B1 | 3/2001 | Bender et al. | |
| 6,258,084 B1 | 7/2001 | Goldman et al. | |
| 6,273,885 B1 | 8/2001 | Koop et al. | |
| 6,287,271 B1 * | 9/2001 | Dubrul et al. | 604/22 |
| 6,413,253 B1 | 7/2002 | Koop et al. | |
| 6,451,007 B1 | 9/2002 | Koop et al. | |
| 6,508,782 B1 * | 1/2003 | Evans et al. | 604/22 |
| 6,547,754 B1 * | 4/2003 | Evans et al. | 604/22 |

(Continued)

OTHER PUBLICATIONS

U.S. Appl. No. 10/335,176, filed Dec. 2002, by Baumgardner et al.

(Continued)

*Primary Examiner* — Andrew Iwamaye
(74) *Attorney, Agent, or Firm* — Ray K. Shahani, Esq.; Kin Hung Lai

(57) ABSTRACT

A device and method to improve the ultrasound visibility of a catheter placed inside the body is described. The catheter is sonically vibrated by an external driver device that transmits the acoustic vibration down the catheter and inside the body. An ultrasound transducer is used to pick up the ultrasound vibrations directly or detects the sonic vibrations using a Doppler mode ultrasound machine.

10 Claims, 3 Drawing Sheets

U.S. PATENT DOCUMENTS

| | | | |
|---|---|---|---|
| 6,761,826 B2 | 7/2004 | Bender et al. | |
| 6,936,025 B1* | 8/2005 | Evans et al. | 604/22 |
| 7,862,575 B2* | 1/2011 | Tal | 606/159 |
| 7,921,854 B2* | 4/2011 | Hennings et al. | 128/898 |
| 7,967,834 B2* | 6/2011 | Tal et al. | 606/159 |
| 2003/0083608 A1* | 5/2003 | Evans et al. | 604/22 |
| 2003/0191460 A1* | 10/2003 | Hobbs et al. | 606/15 |
| 2004/0030263 A1* | 2/2004 | Dubrul et al. | 600/565 |
| 2004/0249401 A1* | 12/2004 | Rabiner et al. | 606/159 |
| 2005/0055040 A1* | 3/2005 | Tal | 606/159 |
| 2005/0131400 A1* | 6/2005 | Hennings et al. | 606/15 |
| 2007/0055326 A1* | 3/2007 | Farley et al. | 607/96 |
| 2007/0282359 A1* | 12/2007 | Tal | 606/159 |
| 2009/0270889 A1* | 10/2009 | Tal et al. | 606/159 |
| 2011/0066142 A1* | 3/2011 | Tal et al. | 606/1 |

OTHER PUBLICATIONS

U.S. Appl. No. 10/351,273, filed Jan. 2003, by Hennings et al.
U.S. Appl. No. 10/699,212, filed Oct. 2003, by Hennings et al.
U.S. Appl. No. 08/631,800, filed Apr. 1996, by Hennings et al.
U.S. Appl. No. 10/738,384, filed Dec. 2003, by Hennings et al.
U.S. Appl. No. 11/131,577, filed May 2005, by Hennings et al.
U.S. Appl. No. 09/185,490, filed Jul. 2000, by Koop et al.
U.S. Appl. No. 09/135,330, filed Jul. 1998, by Koop et al.
U.S. Appl. No. 09/134,776, filed Aug. 1998, by Koop et al.
U.S. Appl. No. 10/160,579, filed May 2002, by Koop et al.
U.S. Appl. No. 10/031,154, filed Jan. 2005, by Koop et al.
U.S. Appl. No. 08/482,208, filed Jun. 1995, by Hennings et al.; and.
U.S. Appl. No. 11/612,324, filed Dec. 18, 2006 by Hennings et al.

* cited by examiner

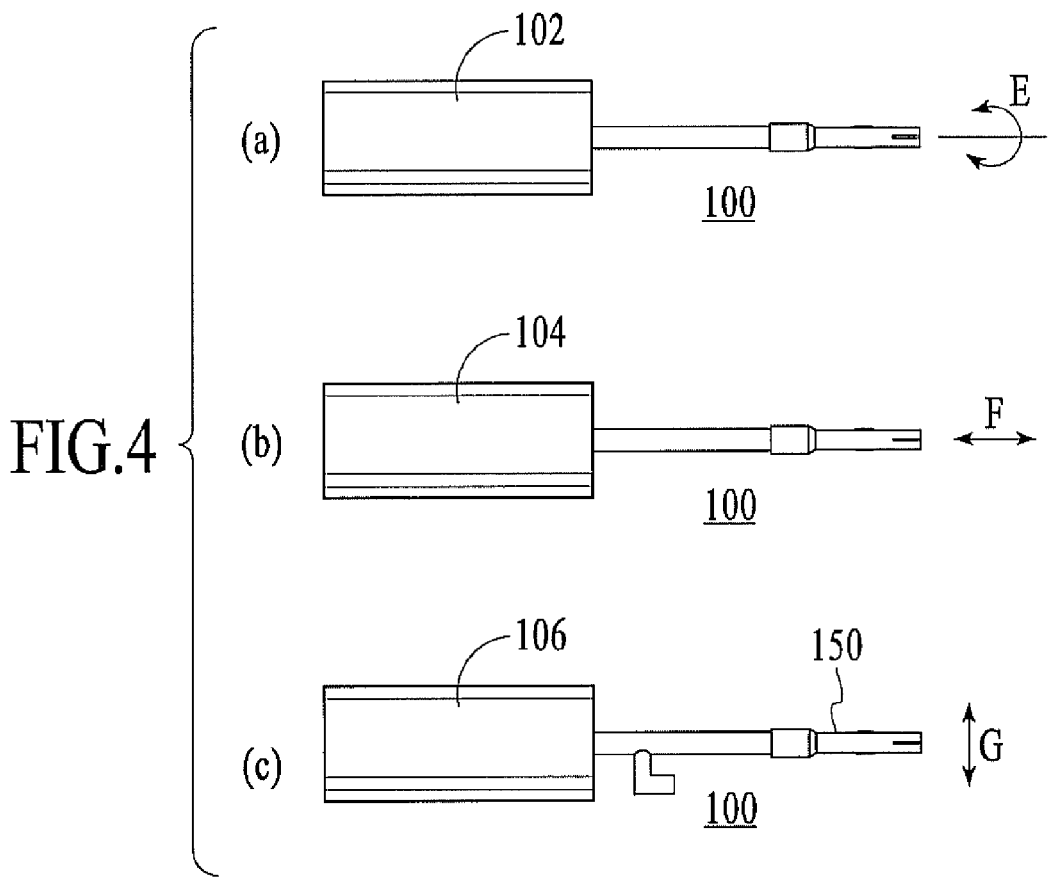
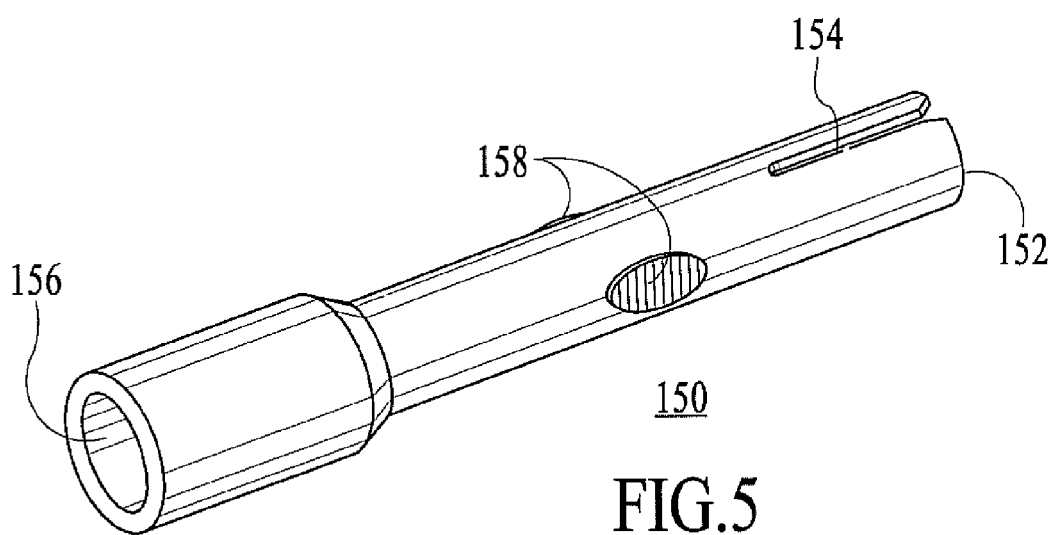

SONIC ENDOVENOUS CATHETER

RELATED APPLICATIONS

This application is related to pending U.S. Provisional Patent Application Ser. No. 60/864,101 filed Nov. 2, 2006 entitled SONIC ENDOVENOUS CATHETER, which is incorporated herein by reference in its entirety, and claims any and all benefits to which it is entitled therefrom.

FIELD OF THE INVENTION

This device is related to imaging of catheter devices placed inside the body for the diagnosis or treatment of internal diseases. This device is also used to reduce the perceived pain of tumescent anesthesia injections and to induce vein spasm when treating venous disease to help drain the vessel of blood.

BACKGROUND OF THE INVENTION

Ultrasound and ultrasonic imaging has made great advances in recent years do to improved transducers, computer analysis of the return signal and the incorporation of Doppler analysis of the image. US equipment is standard equipment in all hospitals and many clinics. The use of ultrasound is critical for locating catheters in veins during endovascular procedures. In most cases the resolution and gain of current equipment is sufficient to see the catheter and interpret the image, although it is common to use a specially trained technician to operate the device because it does require training and skill that few doctors have. The Doppler mode on these ultrasound machines is typically used to show movement of blood in veins or arteries. The Doppler frequency shift of sound that reflects of moving objects is displayed with a color on the ultrasound image that shows tissue or blood movement. The intensity and duration of this movement can be used to diagnose reflux in leg veins that are caused by incompetent valves and result in varicose veins.

Doppler is also used to image blood flowing in the heart to show efficiency and functionality of heart valves. When the target structure is very deep in tissue as when imaging veins in the thigh, it can be very hard to resolve the structure. In fact, imaging the end of the catheter is considered to be one of the most difficult parts of an endovenous procedure such as varicose vein treatment. In many cases, if the catheter is not imaged properly it is possible to treat the wrong section of the vein or even the wrong vein causing severe complications or even death. There is a great need to improve the ability to see inside the body. It would be advantageous to enhance the visibility of the location of catheters.

In addition there is a need to drain blood and reduce the diameter of vessels during endovenous ablation for the treatment of varicose veins. This can be accomplished by elevating the leg, applying compression, or injecting vasoconstrictors near the vein. It is also possible to cause the vein to shrink in size and force out blood by stimulating the vein to react in a way that is called a "spasm". This is a natural body reaction to insult or injury that helps protect the venous system. During some types of surgery, particularly endovenous ablation, it helps to try to force the vein to spasm after the catheter is inserted so blood is forced out of the vein that may interfere with the ablation process. The prior art fails to teach a device that is able to vibrate inside the vein at about 500 Hz and tickling the entire internal length of the vein.

Pain management is a big part of the practice of many doctors, especially since more procedures are being done under local anesthesia in the doctor's office instead of in the hospital under general anesthesia. With the patient awake, the practice of certain procedures requires different techniques to prevent the patient from perceiving pain. It has been known that it is possible to distract patients from pain sensations and to stimulate nerves with a secondary sensation that blocks the transmission of a pain. Dentists commonly do this by pinching the cheek prior to injecting anesthesia and the vibrations from a motorized liposuction probe can mask the sensations of a needle penetrating the skin. The prior art fails to teach a way to do this inside the body in previously inaccessible locations by transmitting the distracting vibrations down a catheter or probe to the internal treatment site.

Prior devices to enhance imaging of internal structures using sound energy have concentrated on a couple of techniques:

1. Increasing the acoustic reflectivity of devices inserted into the body.
2. Placing ultrasound transducers on the device inside the body and detecting the emissions externally.
3. Transmitting longitudinal US waves down waveguides into the body and detecting the return waves along the same waveguide.

One major disadvantage of prior art imaging systems is the very low signal to noise ration of the technology. When the device to be imaged has an acoustic reflectivity that is close to that of the surrounding tissue it is very hard to get enough sound to bounce off of it to be imaged. This is especially true for small objects like a fiber optic catheter.

The acoustic density of glass or metal is close enough to that of blood or tissue that a piece of glass is very hard to image. In many cases introducing air into the tip of the catheter is not feasible. Air to tissue has a very large difference in acoustic density so that an air tissue interface reflects sound very well. Many prior art devices use air to enhance imaging.

ADVANTAGES AND SUMMARY OF THE INVENTION

The present invention improves the imaging of the position of devices inside the body. The present invention uses an auxiliary sonic generator to transmit a relatively low frequency acoustic energy at typically 100 to 1000 Hz into the body. The present invention also transmits the energy using transverse mechanical waves and not longitudinal sound waves as all prior ultrasound techniques have utilized.

While devices of the prior art utilize ultrasound detectors to sense the high frequency vibrations directly, the present invention alters the ultrasound detection by imposing a Doppler or frequency shift on the return ultrasound signal. It is this Doppler shifted signal which can easily be imaged. No other parts of the body are moving this speed so the contrast and signal to noise is very high on the imaging system.

In certain embodiments, the present invention may not allow precise imaging of fine details on the internal device. It may only create a reflecting surface that is moving rapidly enough to be detected under a Doppler imaging device. The main advantage of the present system is to generate a locating signal that has a very high signal to noise ratio. The movement potentially blurs out the fine details that are less than the amplitude of the oscillation.

The present invention is a method to enhance visibility of a catheter device during an endovascular treatment. The method includes the steps of vibrating a catheter device, cannula or probe and ultrasonically imaging the catheter device, a cannula, or probe.

The step of vibrating the catheter device, cannula or probe includes providing a rotational, translational or longitudinal movement thereto.

In a method of sonic endovenous catheter of the present invention, the catheter, cannula or probe is vibrated at a frequency of between about 10 Hz and about 3000 Hz.

In a method of sonic endovenous catheter of the present invention, the catheter, cannula or probe is vibrated at a frequency of between about 100 Hz and about 1000 Hz.

In a method of sonic endovenous catheter of the present invention, the catheter, cannula or probe is vibrated at a frequency of about 500 Hz.

In a method of sonic endovenous catheter of the present invention, the vibration frequency and intensity of vibration is adjusted and optimized for maximum visibility using Doppler capability of an ultrasound-imaging machine.

The method of sonic endovenous catheter of the present invention further includes the step of coupling the vibrating device catheter or probe outside the body such that the vibrations are transmitted along the catheter into the body.

In a method of sonic endovenous catheter of the present invention, the vibrating device is built into the catheter or probe and the vibrating is initiated from within the body.

The method of sonic endovenous catheter of the present invention further includes the step of removably coupling the catheter to be vibrated to a hand-piece that incorporates the vibrator.

The present invention is also a method for inducing vein spasm. The method includes the step of vibrating a device inside a vein.

The present invention is also a method for forcing blood out of a vein during endovascular treatment. The method includes the steps of vibrating a catheter or probe inside a vein and inducing vein spasm, such that the vein spasm temporarily reduces the diameter of the vein.

The present invention is also a method for reducing pain. The method includes the step of vibrating a catheter, a cannula or other functional probe endoscopically placed inside a vein.

The method of sonic endovenous catheter of the present invention further includes the step of timing the vibrations to distract the patient and overwhelm the nerves in the area of treatment to reduce the sensation of pain in the area of treatment.

The method of sonic endovenous catheter of the present invention further includes the step timing the vibrations are timed to distract the patient and overwhelm nerves in the area of treatment and injecting local anesthesia or tumescent anesthesia.

The present invention is also a method for reducing pain associated with the endoscopic insertion and/or moving of a catheter, cannula or other functional probe. The method includes the step of vibrating the catheter, cannula or other functional probe placed inside a vein.

The present invention is also a system for enhancing an endoscopic therapeutic treatment. The system includes an endoscopic catheter, cannula or other functional probe having a predetermined length, a vibration emitter for emitting transverse wave vibrations along the catheter, cannula or other functional probe, apparatus for coupling the vibration emitter to the catheter, cannula or other functional probe, wherein transverse waves are transmitted along the length thereof.

In the sonic endovenous catheter system of the present invention, the amplitude of the vibrations emitted by the vibration emitter can be selected manually.

In the sonic endovenous catheter system of the present invention, the amplitude of the vibrations emitted by the vibration emitter can be pre-programmed.

In the sonic endovenous catheter system of the present invention, the frequency of the vibrations emitted by the vibration emitter can be selected manually.

In the sonic endovenous catheter system of the present invention, the frequency of the vibrations emitted by the vibration emitter can be pre-programmed.

In the sonic endovenous catheter system of the present invention, the vibration emitter operates at a rate of between about 10 and about 3000 Hz.

In the sonic endovenous catheter system of the present invention, the vibration emitter operates at a rate of between about 100 and about 1000 Hz.

In the sonic endovenous catheter system of the present invention, the vibration emitter operates at a rate of about 500 Hz.

In the sonic endovenous catheter system of the present invention, the vibration emitter comprises a motor selected from the group consisting of oscillating motors, rotary and other stepper motors, galvanometers, linear motors and out of balance or eccentrically weighted motors.

In the sonic endovenous catheter system of the present invention, the vibration emitter transmits linear motion to the catheter, cannula or other functional probe.

In the sonic endovenous catheter system of the present invention, the vibration emitter transmits rotational motion to the catheter, cannula or other functional probe.

In the sonic endovenous catheter system of the present invention, the vibration emitter transmits sinusoidal motion to the catheter, cannula or other functional probe.

In the sonic endovenous catheter system of the present invention, the endoscopic catheter, cannula or other functional probe comprises an optical fiber having a diameter between about 100 um and about 1000 um.

Further details, objects and advantages of the present invention will be come apparent through the following descriptions, and will be included and incorporated herein.

BRIEF DESCRIPTION OF THE DRAWINGS

FIG. 4 are representative drawings showing how three vibration generators 100 can work using a rotary stepper motor, a galvanometer, a linear motor and an out of balance weight according to the devices and methods of the present invention.

FIG. 5 is a representative top view of one embodiment of sterile disposable clip 150 according to the devices and methods of the present invention.

DETAILED DESCRIPTION OF THE PREFERRED EMBODIMENT

Figure 1:
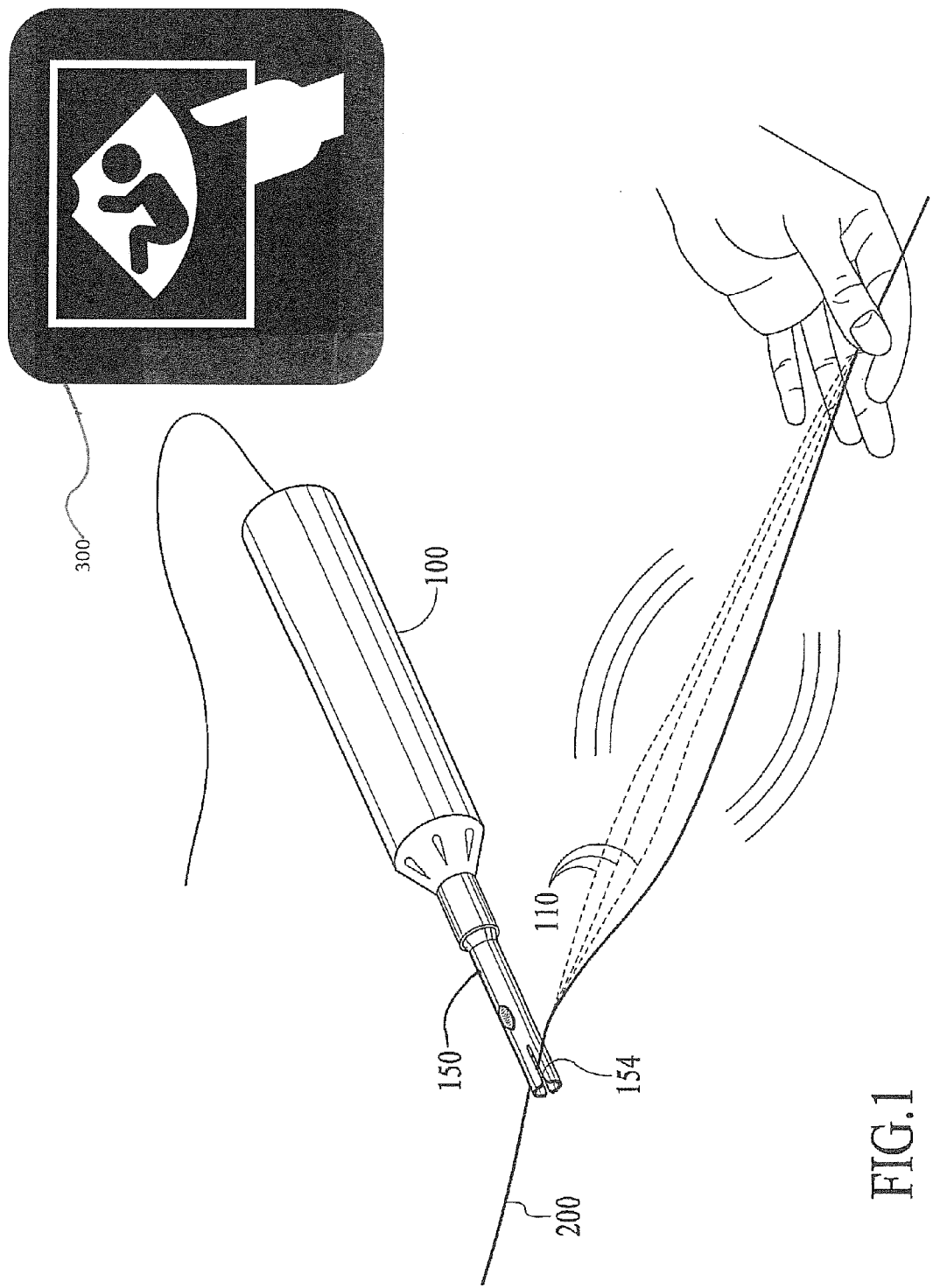
FIG. 1 is a representative drawing of an oscillating motorized device 100 clipped to a catheter 200 to produce rotational vibrations and transverse waves 110 in the catheter 200 according to the devices and methods of the present invention.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

Figure 2:
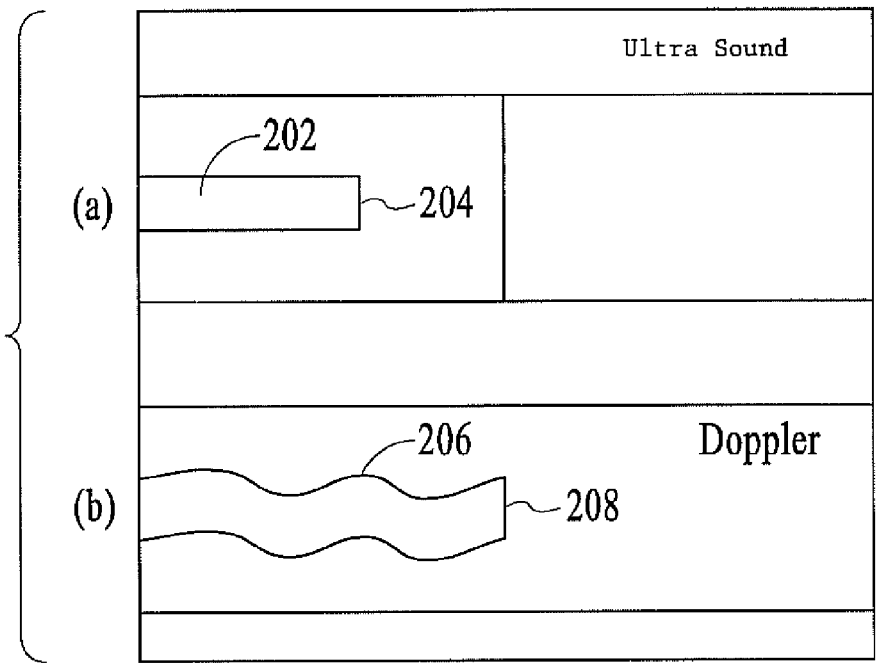
FIG. 2 is a representative drawing of the catheter 200 image on an ultrasound machine with and without vibrations 110 according to the devices and methods of the present invention.

FIG. 1 is a representative drawing of an oscillating motorized device 100 clipped to a catheter 200 to produce rotational vibrations and transverse waves 110 in the catheter 200 according to the devices and methods of the present invention. FIG. 2 is a representative drawing of the catheter 200 image on an ultrasound machine with and without vibrations or transverse waves 110 according to the devices and methods of the present invention.

Apparatus:

As best shown in FIG. 1 and FIG. 2, an embodiment of the present invention requires three parts:
1. A catheter 200 or probe that is rigid and strong enough to vibrate in a transverse manner without degrading.
2. A mechanical vibrating device 100 that moves the proximal end of the catheter a sufficient distance to generate vibrations or transverse waves 110 that propagate the length of the catheter 200.
3. An ultrasound-imaging machine 300 that has a Doppler mode to view the moving catheter 200 inside the body.

In one embodiment, catheter 200 can be an electrical wire assembly that is used to transmit electrical or radio frequency current. The construction can use fine wires that are flexible enough to withstand repeated vibrations without breaking. In alternative embodiments, catheter 200 can also be made of optical quartz, silica or other transparent materials. In one embodiment, catheter 200 should be thin enough to vibrate readily without causing internal bending stresses and should have protective jacket material over the silica to add strength. Many fiber optic catheters 200 used to deliver laser energy are constructed in a manner that will survive such mechanical vibrations 110.

The probe can also be a hollow cannula such as a long needle or tube or a rigid shaft or mechanical device such as used for obtaining biopsy samples.

FIGS. 3a, 3b, 3c and 3d are representative drawings of the end view 152 of the motorized vibrating device 100 showing the clip 150 to the catheter 200 and three possible motions that will cause the entire catheter 200 to vibrate according to the devices and methods of the present invention. FIG. 4 are representative drawings showing how three vibration generators 100 can work using a rotary stepper motor, a galvanometer, a linear motor and an out of balance weight according to the devices and methods of the present invention.

FIG. 5 is a representative top view of one embodiment of sterile disposable clip 150 according to the devices and methods of the present invention. Sterile disposable clip 150 has a proximal end 156 which couples to the oscillating motor 100, and a distal end groove 154 which clips the distal end 152 of the sterile disposable tip 150 to the catheter 200. In one embodiment, sterile disposable clip 150 further has one or more finger grip(s) 158 for conveniently connecting sterile disposable clip 150 to oscillating motor 100.

A transverse wave 110 is one in which the direction of displacement at each point of the medium is parallel to the wavefront, or a wave in which the vibration is moving in a direction perpendicular as that in which the wave is traveling. In a transverse wave the medium moves at right angles to the wave direction. For example: if a wave moves along the x-axis, its oscillations are in the y-z plane. In other words, it oscillates across the 2-dimensional plane that it is traveling in. It may oscillate either vertically or horizontally, and this refers to its polarity. Water waves are an example of transverse waves. Electromagnetic waves are also transverse waves.

Figure 3:
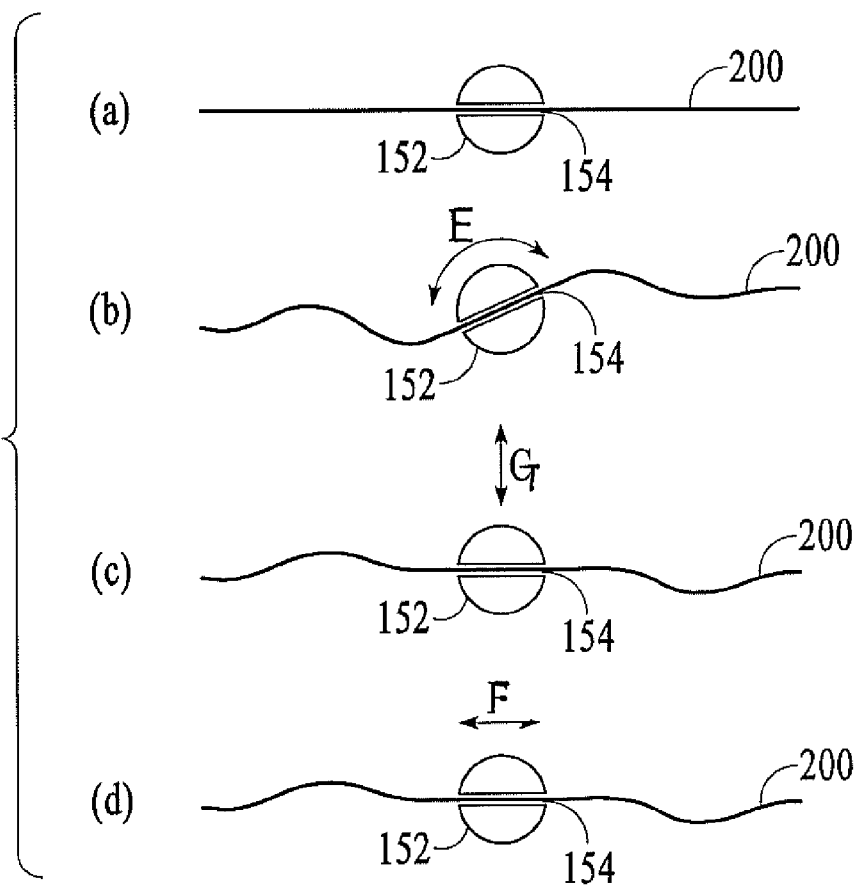
FIG. 3 are a representative drawings of the end view 152 of the motorized vibrating device 100 showing the clip 150 to the catheter 200 and three possible motions that will cause the entire catheter 200 to vibrate according to the devices and methods of the present invention.

As best shown in FIG. 3 and FIG. 4, the mechanical vibrating device 100 can operate in several modes to generate transverse wave motion 110 in the catheter 200. As best shown in FIG. 3b and FIG. 4a, in one embodiment, a rotary motion E can be used to twist the catheter 200 back and forth through about plus or minus 15 degrees. In one embodiment, a rotary motion E can be generated by a stepper motor 102 such as available from AMCI or Danaher Motion which is stepped back and forth through one step. An electronic galvanometer such as available from General Scanning can be used which has a shaft that is connected to electromagnets in a coil. When alternating current is applied to the coils the shaft will oscillate through a small angle in either a driven or a resonant fashion. A stepper motor 102, where an internal rotor containing permanent magnets is controlled by a set of external magnets that are switched electronically. A stepper motor 102 is a cross between a DC electric motor and a solenoid. A stepper motor 102 is a type of electric motor which is used when something has to be positioned very precisely or rotated by an exact angle. Simple stepper motors 102 "cog" to a limited number of positions, but proportionally controlled stepper motors can rotate extremely smoothly. Computer controlled stepper motors 102 are one of the most versatile forms of positioning systems, particularly when part of a digital servo-controlled system. In a stepper motor 102, an internal rotor containing permanent magnets is controlled by a set of stationary electromagnets that are switched electronically. Hence, it is a cross between a DC electric motor and a solenoid. Stepper motors 102 do not use brushes and commutators. Stepper motors 102 have a fixed number of magnetic poles that determine the number of steps per revolution. Most common stepper motors 102 have 200 full steps/revolution, meaning it takes 200 full steps to turn one revolution. Advanced stepper motor 102 controllers can utilize pulse-width modulation to perform microsteps, achieving higher position resolution and smoother operation. Some microstepping controllers can increase the step resolution from 200 steps/rev to 50,000 microsteps/rev. Stepper motors 102 are rated by the torque they produce. A unique feature of steppers is their ability to provide position holding torque while not in motion. To achieve full rated torque, the coils in a stepper motor 102 must reach their full rated current during each step. Stepper motor 102 drivers must employ current regulating circuits to realize this. The voltage rating (if there is one) is almost meaningless. Computer controlled stepper motors 102 are one of the most versatile forms of positioning systems, particularly when digitally controlled as part of a servo system.

In an alternative embodiment, as best shown in FIG. 4b, a linear motion F can be produced by a linear motor 104. A linear motor 104 is essentially an electric motor that has been "unrolled" so that instead of producing a torque (rotation), it produces a linear force along its length by setting up a traveling electromagnetic field. Linear motors 104 are most commonly induction motors or stepper motors. You can find a linear motor in a maglev (Transrapid) train, where the train "flies" over the ground.

In yet another alternative embodiment, as best shown in FIGS. 3c and 4c, a up and down motion G can be produced by an out of balance arc motor 106.

Methods of Use:

FIG. 2 is a representative drawing of the catheter 200 image on an ultrasound machine with and without vibrations 110 according to the devices and methods of the present invention. An embodiment of an imaging procedure is as follows:

FIG. 2 is a representative drawing of the catheter 200 image on an ultrasound machine with and without vibrations 110 according to the devices and methods of the present invention. An embodiment of an imaging procedure is as follows:

1. The Ultrasound Imaging device such as made by GE, or others is placed over the section of body of interest. For example, in the case of performing endovascular laser ablation to treat varicose veins, the transducer head of the ultrasound device could be placed to image the saphenofemoral junction (SFJ).
2. Insert the catheter 200 into the vein from an access point near the knee and move it toward the SFJ. It is critical that the ablation catheter 200 be placed precisely 1-2 cm below this junction or damage to femoral vein could occur with severe consequences to the patient. Using conventional, passive ultrasound, it is usually very hard to see the image of the catheter 202 or the catheter tip 204 at this site as best shown in FIG. 2(a).
3. Attach the external sonic vibrator device 100 described above to the catheter 200 just outside the access point to the vein, and turn on to vibrate the catheter 200 in a transverse manner down through the vein to the tip. Switch the ultrasound-imaging machine to Doppler mode, as best shown in FIG. 2(b), and look for the characteristic color pattern 206 created by moving objects. Move the catheter 200 slowly in and out until the color pattern is properly positioned.
4. The intensity of the color Doppler pattern 206 may be adjusted by changing the external vibration 110 frequency or intensity. It is advantageous to not overwhelm the image of the vein at the same time but to adjust the signal strength so that the tip of the catheter 208 and the vein are both visible at the same time.

Experimental Results:

A branched vessel phantom made by Advanced Medical Technologies, Select Series Branched 4 Vessel Vascular Access Phantom by Blue Phantom PN BPBV110, filled with water was used to simulate a vein inside the body. A 600 um endovenous ablation catheter was placed in one of the vein lumens through a silicone tube to simulate vein transmission. A Diasonics Spectra Plus ultrasound-imaging machine with a 5 MHz linear array coupled with gel was used to image the catheter in the phantom. After the vein was located in the phantom under ultrasound, the catheter was inserted to the desired location. The gain on the ultrasound was reduced until the catheter was no longer visible to simulate imaging deep within the body. An oscillating motor was attached to the catheter about 24 inches from the imaging site. The motor rotated through 30 degrees of movement at about 500 Hz causing the catheter to vibrate in large standing waves that had about 5 mm of amplitude outside the phantom. Inside the phantom it was estimated that the catheter moved approximately 1 mm in a transverse vibration. Under ultrasound with the Doppler mode, this movement was seen as a large colored area that had a distinct end point to it. After the gain of the ultrasound was reduced, it was possible to see exactly where the catheter was located. The end of the catheter signal moved in and out clearly with catheter movement from outside.

Subsequently, the catheter was "life tested" to determine the fatigue that the vibrations may impose on the catheter. The catheter, a 600 um quartz endovenous probe, was vibrated for an additional one hour without any signs of degradation. The vibration time in vivo should be a minute or less. The simulated life test was considered successful, and further testing will determine mean time before failure, usable life expectancy, etc. Tests also show that the 365 um fiber works better inside the leg than the thicker 600 um fiber.

Guideline for the Use of Sonic Vibrator

Pre Operation:

1. Make sure that handle is charged. A full charge will last for about 30 mm of use as indicated by 3 or more green leds on the handle.
2. Sterilize fiber clip by autoclaving in pouch for 270 degrees F. for 3 mm. or 250 deg F. for 15 mm.

Sterile Field:

1. Place sonic handle in sterile Ultrasound probe bag.
2. Place fiber clip onto handle through sterile bag. Make sure that it is tight onto handle.
3. Advance fiber through sheath in vein until it is approximately at the proper place.
4. Set Ultra Sound to doppler mode and image the location.
5. Choose a location on the fiber about 2 inches outside sheath to place the sonic vibrator.
6. Slide the fiber into the slot at the end of fiber clip making sure that it is fully engaged and tight in the slot
7. Press light green "ON" button on the sonic handle to vibrate fiber. It may be necessary to tape or hold the free side of the fiber to prevent it from vibrating excessively outside the leg. The fiber should stay attached in the slot in the fiber clip. If it falls out, push it back in.
8. The sonic handle may turn off by itself in about 1 minute. Simply press the light green button to re start it. The handle may also pause occasionally but re-start by itself.
9. Locate the end of the fiber by locating the color pattern generated by the Doppler image. Turn down the gain of the US if necessary to get better resolution. The tip of the fiber should show as a clean end to the color return. Move the fiber in or out of the sheath to position the fiber in the vein.
10. Turn the sonic handle off by pressing the light green button again and remove the fiber from the holder.
11. Slip a white donut marker over the fiber at the end of the sheath to mark the fiber position.
12. Proceed with the endovenous ablation.
13. The fiber clip may be reused.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method for inducing vein spasm while performing endovascular laser ablation to treat varicose veins under visualization comprising:
   introducing an endoscopic catheter, cannula or other functional probe having a tip and a length into a vein, wherein the endoscopic catheter, cannula, or other functional probe comprises an optical fiber;
   coupling a vibration emitter to the catheter, cannula or other functional probe;
   using the vibration emitter to vibrate the catheter, cannula, or other functional probe such that transverse wave vibrations are generated along the catheter, cannula, or other functional probe that propagate the length of the catheter, cannula, or other functional probe at a frequency of between 10 and 3000 Hz inside the vein such that the vein spasms forcing blood out of the vein and temporarily reducing the diameter of the vein;
   visualizing the tip of the catheter, cannula or other functional probe; and
   delivering laser energy from the catheter, cannula, or other functional probe to the vein.

2. The method of claim 1 further comprising
   manually selecting an amplitude of the transverse wave vibrations generated by the vibration emitter.

3. The method of claim 1 further comprising a:
   manually selecting a frequency of the transverse wave vibrations generated by the vibration emitter.

4. The method of claim 1 in which the catheter, cannula, or other functional probe is vibrated at a frequency of between 100 and 1000 Hz.

5. The method of claim 1 in which the catheter, cannula, or other functional probe is vibrated at a frequency or 500 Hz.

6. The method of claim 1 further comprising:
   selecting the vibration emitter from the group consisting of oscillating motors, rotary and other stepper motors, galvanometers, linear motors and out of balance or eccentrically weighted motors.

7. The method of claim 1 wherein the optical fiber has a diameter between 100 um and 1000 um.

8. The method of claim 1 further comprising:
   visualizing the tip of the catheter, cannula or other functional probe using Doppler shifted ultrasound imaging.

9. A method for inducing vein spasm while performing endovascular laser ablation to treat varicose veins under visualization comprising steps of:
   introducing an endoscopic catheter, cannula or other functional probe having a tip and a length into a vein, the catheter, cannula, or other functional probe configured to deliver laser energy;
   coupling a vibration emitter to the catheter, cannula or other functional probe;
   using the vibration emitter to vibrate the catheter, cannula, or other functional probe such that transverse wave vibrations are generated in the catheter, cannula, or other functional probe that propagate the length of the catheter, cannula, or other functional probe at a frequency of between 10 and 3000 Hz inside the vein such that the vein spasms, thereby forcing blood out of the vein and temporarily reducing the diameter of the vein;
   visualizing the tip of the catheter, cannula or other functional probe; and
   delivering laser energy from the catheter, cannula, or other functional probe to the vein.

10. The method of claim 9 further comprising:
    visualizing the tip of the catheter, cannula or other functional probe using Doppler shifted ultrasound imaging.

* * * * *